United States Patent
Prystupa et al.

(10) Patent No.: US 8,227,719 B2
(45) Date of Patent: Jul. 24, 2012

(54) REMOVAL OF FUSARIUM INFECTED KERNELS FOR GRAIN

(75) Inventors: David A. Prystupa, Pinawa (CA); Jennifer Powell, Pinawa (CA); Matthew Allen, Pinawa (CA); Chris Vogt, Pinawa (CA)

(73) Assignee: Spectrum Scientific Inc., Pinawa, MB (CA)

( * ) Notice: Subject to any disclaimer, the term of this patent is extended or adjusted under 35 U.S.C. 154(b) by 29 days.

(21) Appl. No.: 12/997,923

(22) PCT Filed: Jun. 25, 2009

(86) PCT No.: PCT/CA2009/000886
§ 371 (c)(1),
(2), (4) Date: Dec. 14, 2010

(87) PCT Pub. No.: WO2009/155706
PCT Pub. Date: Dec. 30, 2009

(65) Prior Publication Data
US 2011/0094946 A1    Apr. 28, 2011

Related U.S. Application Data

(60) Provisional application No. 61/129,451, filed on Jun. 27, 2008.

(51) Int. Cl.
*B07C 5/342* (2006.01)
(52) U.S. Cl. .................. 209/587; 209/577; 209/938
(58) Field of Classification Search .............. 209/576, 209/577, 587, 938; 356/446, 448
See application file for complete search history.

(56) References Cited

U.S. PATENT DOCUMENTS

| 4,037,970 A | * | 7/1977 | Webster et al. ............... 356/418 |
| 5,241,178 A | * | 8/1993 | Shields ..................... 250/339.02 |
| 5,308,981 A | * | 5/1994 | Perten ...................... 250/339.11 |
| 5,865,990 A | | 2/1999 | Novak et al. |
| 6,014,451 A | * | 1/2000 | Berry et al. .................... 382/110 |
| 6,100,526 A | | 8/2000 | Mayes |

(Continued)

FOREIGN PATENT DOCUMENTS

CA    2241471    12/1998

(Continued)

OTHER PUBLICATIONS

International Search Report issued in corresponding International Application No. WO/2009/155706, Aug. 25, 2009.

*Primary Examiner* — Joseph C Rodriguez
(74) *Attorney, Agent, or Firm* — Paul S. Sharpe

(57) ABSTRACT

Fusarium infected grain is separated by comparing reflected and transmitted light at two wavelengths, one at which the light is substantially reflected and scattered the same by healthy and infected kernels, the other at which the light is reflected and scattered to a significantly greater degree by infected than healthy kernels. An apparatus having a rotating apertured cylinder, with a low internal vacuum, allows comparison of individual kernels. When comparison indicates that a kernel is infected, a lever dislodges it from the cylinder allowing it to fall into a receptacle for infected kernels. Kernels remaining on the cylinder are scraped off to fall into a receptacle for healthy kernels. Although results vary, to some extent depending on the degree of infection, approximately 90% of healthy kernels and 5% of infected kernels are deemed "healthy", while approximately 10% of healthy kernels and 95% of infected kernels are deemed "infected," reducing the level of infected kernels.

10 Claims, 6 Drawing Sheets

U.S. PATENT DOCUMENTS

| | | |
|---|---|---|
| 6,483,583 B1 | 11/2002 | Wright et al. |
| 6,646,264 B1 | 11/2003 | Modiano et al. |
| 6,791,683 B2 * | 9/2004 | Sjodin .......................... 356/326 |
| 7,508,517 B2 * | 3/2009 | Wright .......................... 356/432 |
| 7,830,504 B2 * | 11/2010 | Deppermann et al. ........ 356/305 |
| 8,031,910 B2 * | 10/2011 | Jones et al. ................... 382/110 |
| 8,061,527 B2 * | 11/2011 | Koyama et al. ............... 209/539 |
| 2007/0182960 A1 * | 8/2007 | Jayaraman ................... 356/318 |

FOREIGN PATENT DOCUMENTS

| | | |
|---|---|---|
| WO | 2003025858 | 3/2003 |
| WO | 2008124925 | 10/2008 |

* cited by examiner

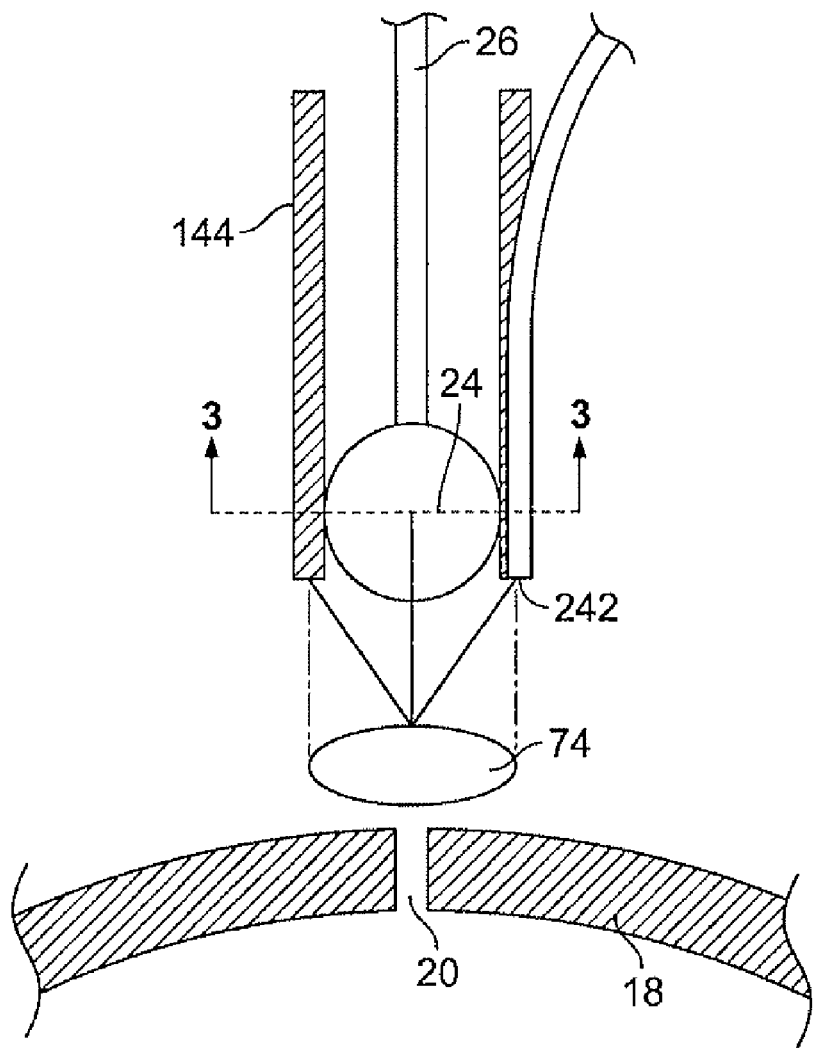
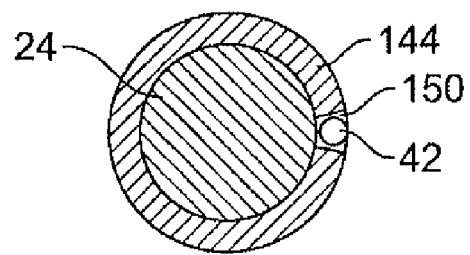
FIG. 3

REMOVAL OF FUSARIUM INFECTED KERNELS FOR GRAIN

TECHNICAL FIELD

The invention is directed to detecting and removing fusarium infected kernels, which contain mycotoxin (such as deoxynivalenol or zearalenone) from grain.

BACKGROUND ART

Generally, the most relevant prior art is found in, application, PCT/CA2008/000667, filed 14 Apr. 2008, publication WO/2008/124925, published 23 Oct. 2008, Prystupa et al. The document discloses a device to detect infected kernels, which had an LED passing light through a collimator consisting of a glass rod about 3 mm diameter and 4 cm long with a 5 mm sphere on its end acting as a focussing lens onto a kernel approximately 6 mm from the sphere. A light receiving device consisted of an array of optical fibre bundles spaced from and surrounding the sphere subtending an inner angle of about 30° from the rod axis and an outer angle of about 60° from the rod axis at the kernel. The optical fibre bundles combined the collected light at a photodiode. This arrangement satisfactorily distinguished infected from healthy kernels by analysis and comparison of reflected light intensity, in practice measuring the kernel shadow was used for normalisation.

DESCRIPTION OF THE INVENTION

The invention is directed to a method and an apparatus to perform the method, to detect and remove infected kernels from grain. Incident light is scattered by the kernel with an infected kernel reflecting and scattering quantitatively differently from a healthy kernel. The amplitude of the reflected and scattered light is measured by a detector and compared to a threshold value derived from statistical analysis of separate samples of known healthy and infected kernels. In the method as developed, when the amplitude is above a threshold value the kernel is considered "infected," when the scattered light falls below the threshold value, the kernel is considered "healthy." The threshold is set so as to minimize the overall amount of mycotoxin in kernels deemed "healthy." "Infected" kernels are then separated from "healthy" kernels.

Although the invention is described and referred to specifically as it relates to a method and an apparatus to perform the method to detect and separate infected grain by comparison of the amplitude of scattered and reflected light, it will be understood that the principles of this invention are equally applicable to similar methods, devices, machines and structures for infected grain separation. Accordingly, it will be understood that the invention is not limited to such methods, devices, machines and structures, for infected grain separation.

Fusarium head blight infects wheat and can affect up to 50% of kernels. As infected wheat has little or no commercial value, effective removal of mycotoxin has significant economic value. 1% infected kernels generally equilibrates to 1 part per million of mycotoxin, the current Canadian maximum for food, while the EU has a maximum of ½ part per million. Wheat is graded in steps of maximum fusarium infected kernels at 0.25%, 0.5%, 1%, 1.5%, 2%, 5%, not all steps are present for each type of wheat, with increasing discounts at higher infection. In Canada more than 5% is graded "fusarium damage," more than 10% "commercial salvage," which depending on market conditions may be sold at very deep discount, or not at all. Mycotoxin content is currently reduced either by sieving the kernels as healthy kernels are larger than infected kernels, or by abrading (removing the kernel surface where the toxin is concentrated) at milling. As a rule of thumb, milling reduces mycotoxin by half at 2 ppm (to 1 ppm) by removing the outer layer of the kernel.

Previous work had showed that there was size variation between healthy and infected kernels, not only are infected kernels smaller than healthy kernels, but infected kernels have lower density.

Testing at 630 nm showed some varieties of wheat had significant differences in reflecting and scattering between healthy and infected kernels, while others had no apparent and consistent differences. It was determined that when individual kernels were normalised by area, calculated as $\frac{2}{3}$rd power of kernel mass, a consistent difference ratio was demonstrable, with the ratio reflected and scattered light being from 1.4 to 1.6 greater from infected than healthy kernels. The difference was statistically significant and noticeable. Kernel area can be directly measured, by the shadow generated by a light beam for instance, and the scattered and reflected light amplitude compared to the measured kernel area. In practice precision measuring equipment was used of the type used in academic level research.

To determine suitable wavelengths a variety of LEDs were used to measure raw and comparative reflectance of healthy and infected kernels from about 400 to 900 nm. The comparison was least sensitive around 500 nm, most sensitive around 450 nm and again from 590 to 650 nm. In practice suitable commercially available LEDS were 505 nm (cyan) and 590 nm (amber). Other wavelengths could be used.

An infected sample of visually identified heavily infected kernels was tested for reflected and scattered light, one standard deviation below the mean was taken as the threshold for rejection. The scattered and reflected light was measured at a wavelength with significant difference between healthy and infected kernels, and compared to the scattered and reflected light at a wavelength with little, preferably no, difference between infected and healthy kernels, the amplitude at the insensitive wavelength corresponded to kernel area. In practice infected kernels reflect and scatter more light even at the insensitive wavelength. Measuring the peakwidth of the reflected and scattered light should give kernel area. This is not the case because the distribution of scattered and reflected light, both different from each other, are also different between healthy and infected kernels, with the infected kernels reflecting and scattering over a wider angle, which is greater the more intensely infected the kernel is (bidirectional reflectance function, known to those skilled in the art). Reflected light is generally maximised when the surface is at right angles to the incident light, while scattered light is generally maximised when the light is at grazing incidence, nearly parallel to the surface. As these characteristics differ between healthy and infected kernels, an experiment was required to ascertain the most sensitive angle, which was found to be about 45°. As each kernel is compared to itself at two wavelengths, a single light collecting device transmitting light at both wavelengths to a single photodiode, or a group thereof, was desirable. Photodiodes vary, as do groups of photodiodes, using the same photodiode(s) to measure light from the same kernel eliminates photodiode variation. Strobing both wavelengths allowed the same photodiode(s) to be used sequentially for the same kernel.

In practice it was found that commercially available photodiodes were not sensitive enough compared to academic level measuring equipment to derive reliable ratios to discriminate between infected and healthy kernels. It was found that plotting amplitudes two dimensionally to give a graph allowed development of statistical criteria through mathematical transformation and parameter optimization was sufficient to discriminate satisfactorily between infected and healthy kernels.

In a broad aspect the invention is directed to a method for removing fusarium infected kernels from grain which comprises: illuminating each kernel with distinct first and second wavelengths of light. The first wavelength is selected from wavelengths reflected and scattered substantially the same by healthy and infected kernels. The second wavelength is selected from wavelengths reflected and scattered significantly greater by infected kernels than healthy. The amplitude of light reflected and scattered at each wavelength by each kernel is measured. The amplitude of light reflected and scattered at first wavelength is compared to the amplitude of light reflected and scattered at second wavelength to determine if a criteria for an infected kernel is met. The kernel is rejected when the criteria for an infected kernel is met.

Preferably the wavelengths illuminating said kernel are alternately strobed, to produce a sequence of amplitudes of both wavelengths, which are transformed mathematically to give a single scalar value, which is then compared to a calibrated threshold scalar derived from statistical analysis of known healthy and infected kernels, to determine if the kernel is infected. The statistical analysis may be principal component analysis. The statistical analysis may be linear discriminant analysis. The measured amplitudes for both wavelengths can then be summed to give separate integrated amplitudes for the kernel at both wavelengths, which taken together give a two dimensional vector, which can be mathematically transformed to give a scalar, which can be compared to a calibrated threshold scalar, derived from statistical analysis of samples of known healthy and infected kernels. Preferably the first wavelength is 505 nm and the second wavelength is 590 nm.

In another broad aspect the invention is directed to an apparatus to separate fusarium infected kernels from healthy kernels of grain, comprising an input chute for grain, and separate output chutes for healthy and infected kernels, and a rotatable cylinder having at least one aperture sized to suctionally engage one kernel. The grain input chute abuts the surface of the cylinder in first position. A light source to provide light to illuminate the kernel at two distinct wavelengths on the surface of the cylinder is in second position, a first wavelength being reflected and scattered substantially the same by healthy and infected kernels, a second wavelength being reflected and scattered significantly differently by healthy and infected kernels. There is means to alternately strobe both wavelengths of the light source. There is a light collector adjacent the light source for collecting the reflected and scattered light at both wavelengths. The light collector transmits the light to a light measuring device comprising at least one photodiode which measures the amplitude of the reflected and scattered light generated by the kernel at both the wavelengths as electronic signals. A microprocessor, compares the electronic signals as measured amplitudes at each wavelength and determines from the comparison whether the kernel meets infected criteria. When the kernel meets infected criteria, the microprocessor transmits a logic signal to actuate a lever integral to a rotary voice coil. The lever when actuated rotates to strike an infected kernel in third position and dislodge it to fall into the chute to receive infected kernels. Scraper means in fourth position dislodges a healthy kernel to fall into the chute to receive healthy kernels. Preferably the light source comprises at least one optical fibre transmitting the wavelengths from a lightbox containing at least one LED generating the first wavelength and at least another LED generating the second wavelength to a lens system collimating and focussing the light to illuminate the kernel. Preferably the microprocessor comprises a field programmable gate array, which controls means to alternately strobe the wavelengths emitted by the light source. Preferably the light measuring device receives the light collector optical fibre onto a plurality of detecting photodiodes to measure the amplitude of the light. An encoder wheel, about 10 cm (4 inch) diameter, is axial with the cylinder. The encoder wheel having at least one aperture therein, and aligned with this encoder wheel aperture is an LED and a photodiode. Light passes through the aperture from the LED to the photodiode, and the photodiode transmits a signal to the means to alternately strobe the wavelengths of the light source, and initiate an alternate strobing sequence.

Preferably the amplitudes are compared as a two dimensional vector of the integrated amplitudes of both wavelengths the criteria for an infected kernel is essentially a location on this graph. The two dimensional vector is mathematically transformed to a scalar. These scalars are compared to scalars derived from statistical analysis of samples of known healthy and infected kernels to provide calibrated scalars. Two derived overlapping normal (gaussian) distributions were found with infected greater than healthy. A scalar threshold is set, if the threshold is equalled or exceeded, the kernel was deemed infected. A logic signal is sent to the rotary voice coil, and the lever dislodges the kernel, which is removed. Various threshold values are possible, that selected rejected about 10% of visually healthy kernels and about 95% of visually infected kernels, overall about 93% of kernels were correctly identified and 7% were not. Depending on the intensity of infection on individual kernels, more or less infected kernels will be rejected, while the proportion of healthy kernels rejected will vary less. Although this is a crude and simplistic measure, it is effective.

Other embodiments of the invention will be apparent to those skilled in the art from the following specification, accompanying drawings and appended claims.

INDUSTRIAL APPLICABILITY

The industrial applicability of the invention lies in detecting and separating fusarium infected kernels from healthy grain kernels, which improves grain quality, increases vendible grain quantity, and food supply.

BRIEF DESCRIPTION OF THE DRAWINGS

FIG. 2 shows a detail of the embodiment of FIG. 1.

FIG. 3 shows a detail of the embodiment of FIG. 1.

BEST MODE FOR CARRYING OUT INVENTION

Figure 1:
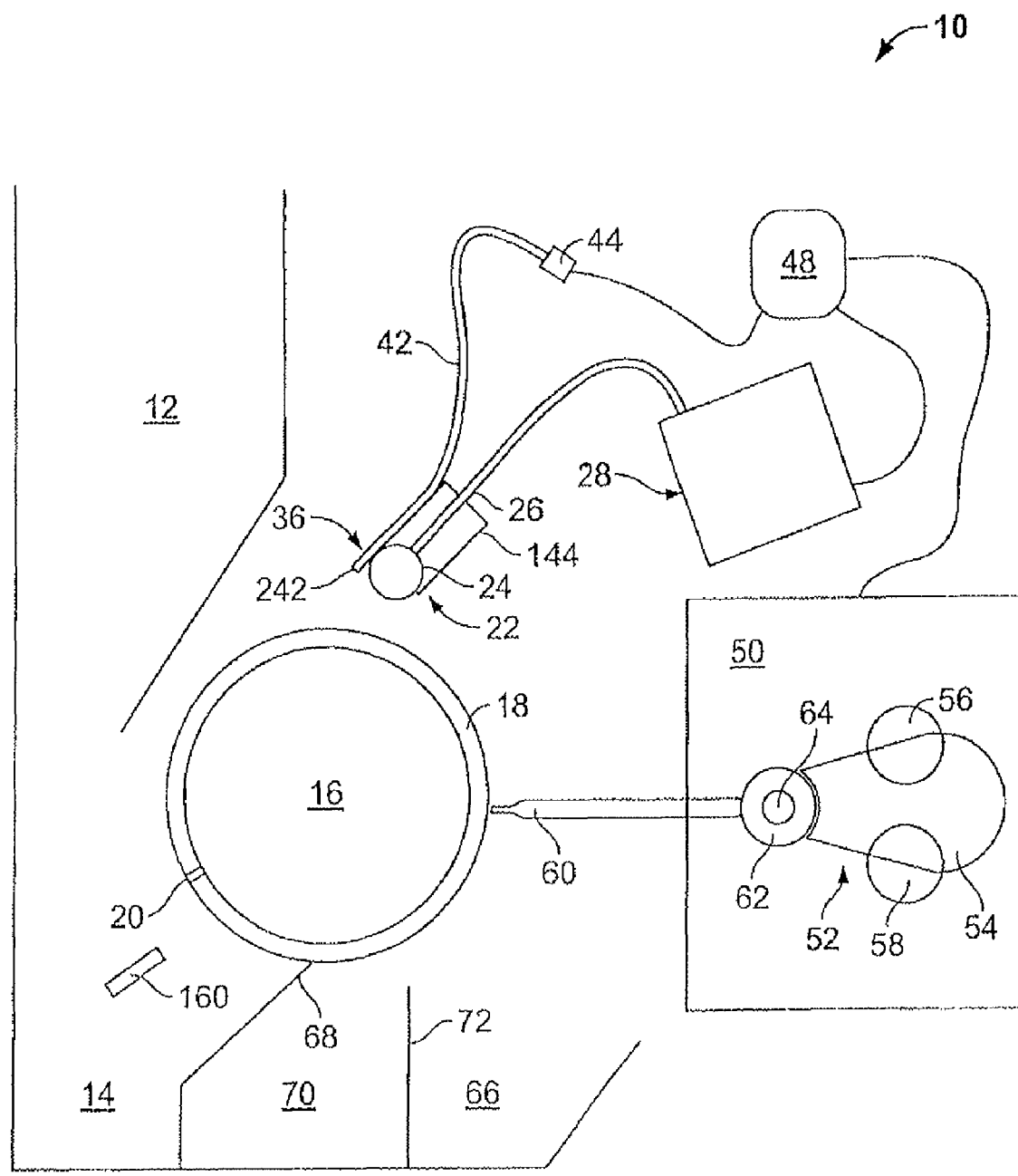
FIG. 1 shows a general side sectional elevational view of an embodiment of the invention.
Figure 4:
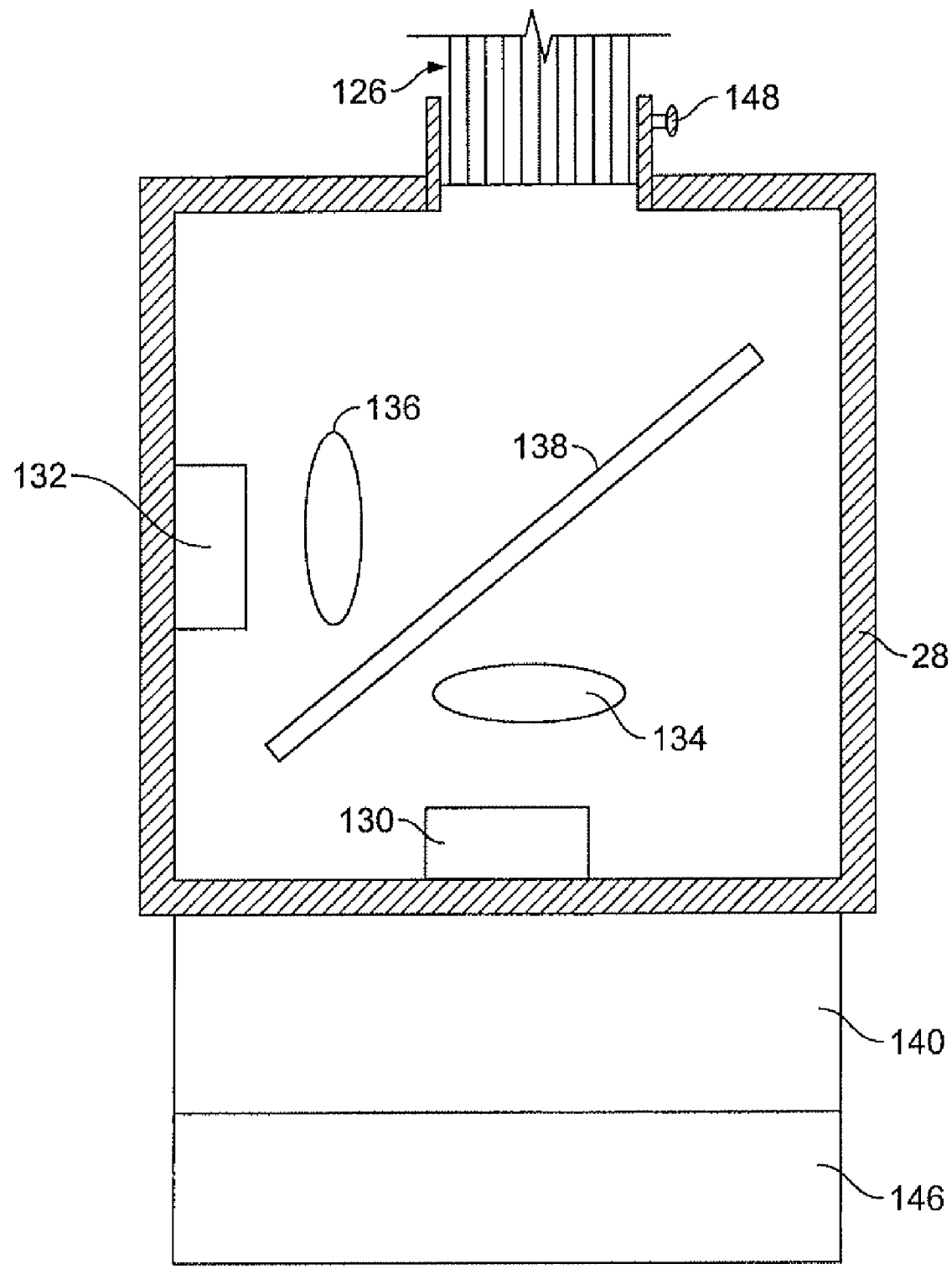
FIG. 4 shows a sectional view of a lightbox of FIG. 1 invention.
Figure 5:
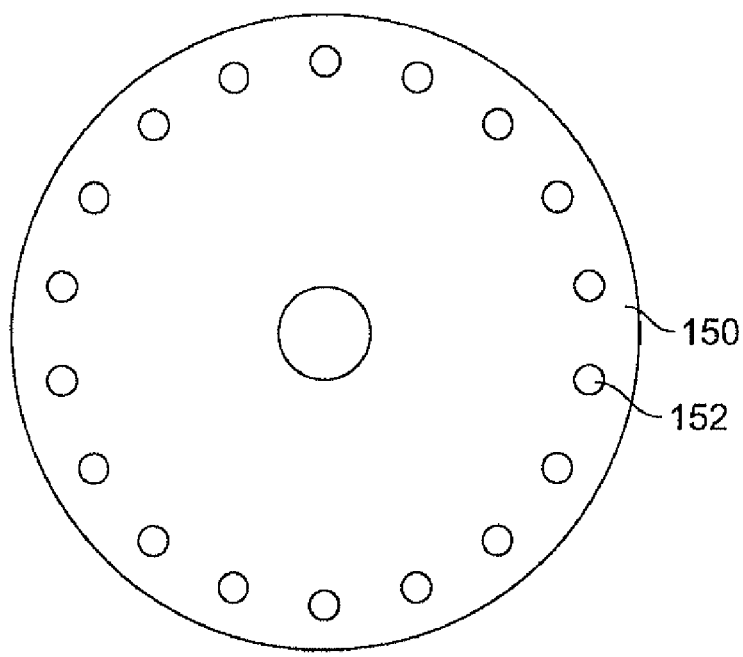
FIG. 5 shows an axial view of an encoder wheel of the invention.
Figure 6:
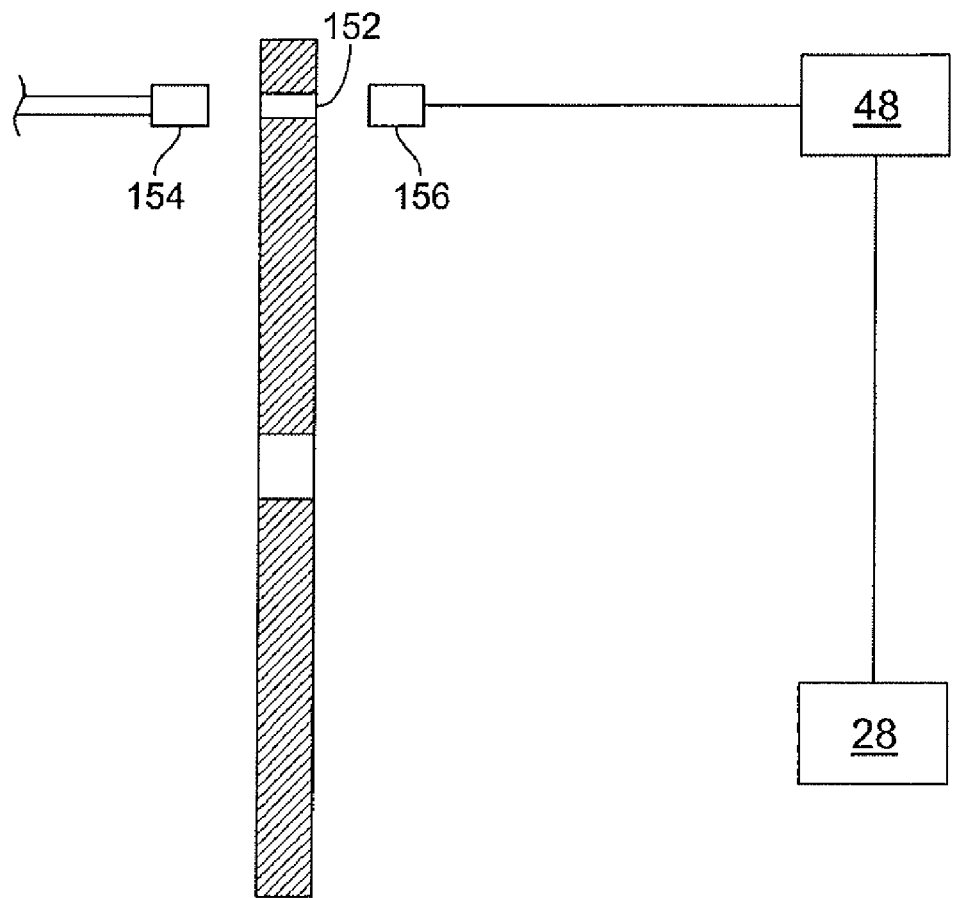
FIG. 6 shows a sectional view of the wheel of FIG. 5.

The invention is described by reference to embodiments which are illustrative and not restrictive in nature. Numeral 10 refers to the entire apparatus. Grain is passed down chute 12 into bin 14, where individual kernels are attracted to cylinder 16, 60 mm diameter, a prototype cylinder some 41 cm (16 inches) has shell 18 about 4 mm thick with an array of apertures 20, by a low internal vacuum, the pressure being at least 3% lower than ambient pressure. Cylinder diameter can be varied, 40 mm was found too small, as kernels not attached to an aperture could be carried upward. Larger cylinders can be used. 60 mm was found convenient. A test prototype was developed it had 18 longitudinal rows of apertures, each row had 32 apertures, the apertures were spaced 12.5 mm (½ inch) apart. A second cylinder 168 cm (5 ft 6 in) long, otherwise identical with longitudinal rows, each of four groups of 32 apertures spaced 12.5 mm centre to centre, with 25 mm (1 inch) gaps between each group, was constructed and found to sag in the middle during rotation. The sag was overcome by providing a central bearing, dividing the cylinder into two 84 cm (32 inch) lengths each with two groups of 32 apertures in each row. The cylinders could also be made from steel, anodized aluminum, or materials of similar tensile strength. Apertures 20 are so spaced that a kernel attached to one does not interfere with another kernel attached to a neighbouring aperture. The dimensions given are specific for wheat and similar sized kernels. Different materials can be accommodated by varying cylinder and hole size and spacing. As shown, cylinder 16 rotates clockwise. Stirrer bar 160 extending longitudinally parallel to cylinder 16, rotates stirring the kernels. The kernels pass under light source 22 and reflect or scatter incident light. Light source 22 emits at two wavelengths, 505 and 590 nm, typically about 6 to 9 mm from the cylinder surface, and about 3 to 5 mm from the kernel surface. The distance can be extended up to 50 mm, more if a laser is used, but is a function of collimation (light focussing). 505 nm is less affected by infected kernels, at 590 nm infected kernels typically reflect 40 to 60% more light. Various other wavelengths can be used. Typically 490 to 540 nm is less affected by infected kernels while other wavelengths, notably 900 nm, are affected to a greater degree. Light source 22 has acrylic ball lens 24 about 9 mm (⅜ inch) or about 6 mm (¼ inch) diameter which collimates and focuses the light onto the kernel. Light is provided by optical fibre 26 from lightbox 28. Generally light is received by an array of 1 mm optical fibre bundles, a 32 fibre bundle was used in the prototype, although 64 optical fibres is envisaged for larger cylinders, each of which can supply one separate light source 22. Although Luxeon LEDs are shown, suitable high powered LEDs are available for the applied wavelengths, LEDs are currently preferred over lasers, as they have a longer life of 100,000 hours as compared to 8,000 hours. Both wavelengths of light are alternately strobed at a frequency of at least 566 Hertz to 2500 Hertz. The lower strobing frequency ensures that there is sufficient reflectance to allow comparison of both wavelengths from one kernel, preferably approximately the same area of the kernel for each wavelength, at the higher strobing frequency LED emission decay becomes significant. In theory, two separate LEDs could be separately mounted in different positions ahead and behind light collector 36, or close together, which is not currently feasible, or two optical fibres each emitting one wavelength, or one optical fibre emitting both wavelengths may be used, the last being preferred as more efficient in power use. In FIG. 4, the light source may consist of a lightbox 28, with one LED of each wavelength, cyan 130, amber 132, and dichroic beamsplitter 138, each LED has a separate collimating lens, 134 and 136 to reduce light output divergence to about 10°. Lightbox 28 has optical fibre bundle 126 clamped by clamp 148, it also has optional heatsink 140 and fan 146. Larger lightboxes with two LEDs of each wavelength may be utilized. Each optical fibre in bundle 126 has a slightly different light input, due to LED output and location. Light collector (collection optics) 36, preferably 6 to 9 mm from the kernel receives the reflected or scattered light. In FIG. 2, the light collector 36 is end 242 of optical fibre 42, 1 mm diameter, attached to tube 144 holding lens 24 of light source 22. It was found that this arrangement was effective. A lens focussing and collimating system, with better optics would produce better results, but the additional cost would probably not be justified. In FIG. 2 light from source 22 is reflected from kernel 74 at about 45° to end 242 of optical fibre 42, lens 24 is about ¼ inch (about 6 mm) diameter, the distance from lens 24 to kernel 74 is typically about 5 or 6 mm, providing an angle around 45°. As shown in FIG. 3 optical fibre 42 is attached to tube 144 and sits in groove 150. The fibre system, although preferred, is not absolutely necessary as the light collecting system can focus light directly on a pixel or photodiode. The same pixel detects both wavelengths, with different sensitivity, and transmits the apparent light amplitude of the wavelengths. Light source 22 is angled at 45° to the kernel light collector 36 axis. It was found that reflection was greatest at 0° diminishing to none at 90°, the difference between the less affected reflectance at 505 nm, and the affected reflectance at 590 nm, increased with angle infected being greater than healthy. <30° the reflected light amplitude was greater but the difference small, >60° the reflected light amplitude was small and the difference greater, the overall signal difference being small. Between 30° and 60°, both reflected light amplitude and the difference give a better overall signal difference, best about 45°. The reflectance or scattering is a function of multiple kernel domains, caused by the surface topology of the kernel, starch granules separated by protein form a solid emulsion, both with different refractive indices, in infected kernels the starch granules are fragmented by fusarium and have changed granule size, and changes of colour in the kernel again caused by fusarium. Light detector 44 consists of a photodiode transmitting a photon count transmitting an analog or digital signal to a logic microprocessor. Light detector 44, TAOS TSL3301-LF has 102 pixels. Light can be transmitted from one or more optical fibres through a focussing lens system, optionally a three lens assembly, to a linear array of photodiodes each optical fibre corresponding to a detecting pixel 85×77 microns, spaced 85 microns centre to centre. In practice detector 44, TAOS TSL3301-LF, first had 16 optical fibres each overlapping 6 pixels, 85 microns across, the fibres are packed with a slight stagger, centres not quite collinear to fit, later 8 optical fibres each overlapping 12 pixels. Direct fibre pixel contact is preferred because it less sensitive to machine vibration. The precise arrangement is not critical, other than that each optical fibre corresponds to an integral number of pixels or photodiodes. The optical fibre diameter is smaller than the integral number of pixels, to ensure each fibre engages a distinct array of pixels. All detectors used are an array of one or more photodiodes or other photon detecting devices. The ones selected are lowest cost CMOS. The detector converts light intensity to an electronic signal. Many other photodiode arrays, CCDs, photomultiplier tubes, and the like, as would be understood by those skilled in the art, can be used for light detection. Given an appropriate lens system, any possible detector could be used with one or more fibres. Detector 44 transmits an analog or digital signal to logic microprocessor 48, which in this case is a field programmable gate array, (FPGA) but may be a computer. The FPGA (Digilent Nexys-2) primarily addresses the TAOS photodiodes with its IO pins. An IO expander can have 128 addresses. Thus one expanded FPGA IO pin, with clock and parity pins, through which its software can address 128 addresses. 32 levers were satisfactorily addressed in the prototype, by the FPGA, but it was tested to ensure that 128 could be satisfactorily addressed. The 505 nm signal and the 590 nm signal are used as joint amplitude indicators. When the amplitudes meet a predetermined threshold the logic processor sends a logic signal other than default, typically 1 as opposed to 0 default, but possibly 0 as opposed to 1 default. The field programmable gate array also puts out the actuating signal for strobing via a switching current regulator (Buck Puck 3021DE1000) system to each light source, and thus can correlate the received apparent amplitude signal with the wavelength. On receiving the logic signal, an H bridge (STMicroelectronics L293D) allows current to flow to ejector 50 actuating rotary voice coil 52, trapezoidal coil 54, of 100 turns of 30 gauge wire, produces a magnetic field which interacting with permanent magnets 56 and 58, of opposed polarity moves arm 60 into active position shown, rotating bearing 62 about shaft 64, displacing a kernel. The current is then reversed moving rotary voice coil 52 to rest position. In rest position, arm 60 is angled upward and heavier rotary voice coil 52 angled downward at about 20°. Rotary voice coil 52 is a smaller version (¾ size) of computer hard drive rotary voice coils. The displaced kernel falls into receptacle 66 for disposal. Undisplaced kernels rotate on cylinder 16 to scraper 68 which displaces them from the cylinder whereupon they fall into receptacle 70 for disposal. Receptacles 66 and 70 are separated by partition 72. Cylinder 16 rotates at about 1.5 revolutions per second, and the displacement position is about 90° from the light station as shown taking the kernel some 167 milliseconds to traverse the distance. The apertured cylinders can be rotated faster or slower, about 1.7 revolutions per second the kernel:aperture ratio declines, that is some apertures do not attract kernels. The rotary voice coil takes about 13 milliseconds to move from rest to active position and the same time to move back. The delay can be calculated then programmed in the logic processor. Or the delay can be estimated and then adjusted by trial and error. In FIG. 5, encoder wheel 150 has 18 equispaced apertures 152, each of which slightly lead an array of apertures 20 and associated kernels. Light from LED 154 passes through aperture 152 to photodiode 156 which transmits signal to FPGA 48 and lightbox 28. This turns on lightbox 28, and starts 24 alternate pulses of both wavelengths, 12 of each colour. These pulses have fast rise time and slow fall time. The light emission of both colours is almost continuous, each pulse lasts about ¾ milliseconds. The amplitude of each colour pulse received at detector 44 is registered during the pulse, and transmitted to the FPGA, in the dead time when the LED switches off between pulses in the alternating sequence. The lightbox and both LEDs switch off after the sequence is complete. The 12 amplitudes of both colours are then processed by mathematical calculation such as LDA, PCA or the like to determine if the kernel is "infected" or "healthy", in the inactive interval. In this sequence, the LEDs only operated about 75% of the time. The exact number of pulses is not critical, it is preferred that the number is sufficient that a kernel aligned with the direction of cylinder rotation is sampled end to end, and that the number is sufficient to adequately sample a kernel. Eight pulses at each wavelength was felt adequate.

Eleven samples of wheat with known mycotoxin levels of 1 to 5 ppm, were run. Mycotoxin was reduced by 84% on average, less at lower levels more at higher. All mycotoxin levels were reduced most to less than 0.5 ppm, two to between 0.5 and 1 ppm.

TABLE I

| Sample | DON ppm before | DON ppm after |
|---|---|---|
| 176 | 2.209 | NIL |
| 107 | 4.514 | 0.728 |
| NH35 | 1.598 | 0.266 |
| 274-25 | 2.276 | 0.201 |
| 242 | 4.000 | 0.185 |
| 265-5 | 2.573 | 0.664 |
| 107-home | 1.822 | 0.377 |
| 257-9 | 1.293 | 0.307 |
| 174 | 0.814 | 0.341 |
| 44 | 0.368 | NIL |
| 268-30 | 3.055 | 0.035 |
| 206-12 | 1.757 | 0.063 |
| 169 | 1.427 | NIL |
| C 1 | 0.420 | 0.181 |
| C 2 | 0.481 | 0.370 |
| C 3 | 0.066 | 0.060 |
| C 4 | 0.261 | 0.300 (increase statistical anomaly) |
| C 5 | 0.008 | NIL |
| C 6 | NIL | 0.059 (increase statistical anomaly) |
| C 7 | 0.017 | 0.099 (increase statistical anomaly) |
| C 8 | 0.037 | 0.028 |
| C 9 | 0.188 | 0.017 |
| C 10 | 0.025 | 0.027 (increase statistical anomaly) |
| AC Superb | 14.162 | 5.032 |
| MBW | 11.663 | 4.145 |

Figure 7:
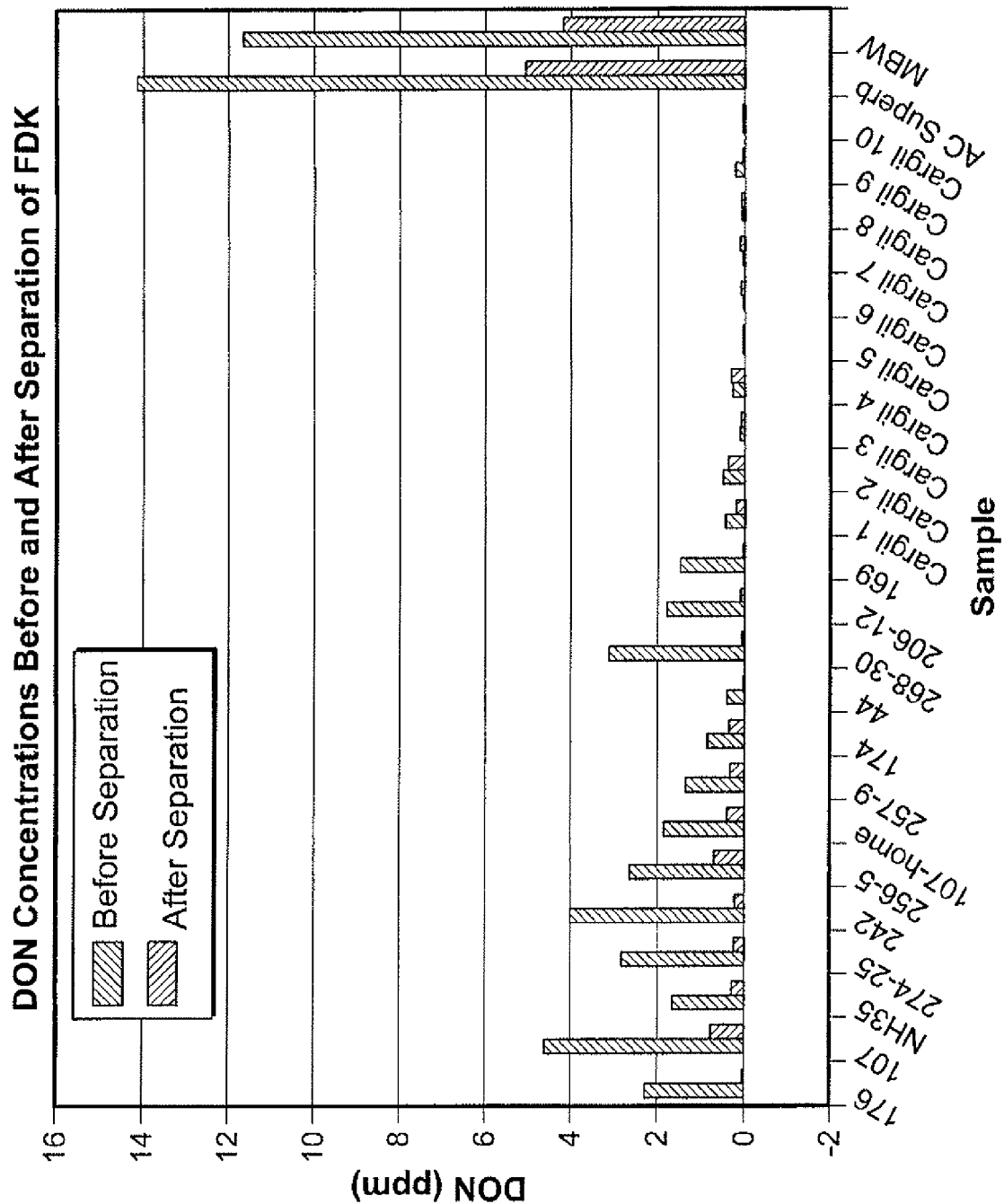
FIG. 7 shows a bar graph of DON (deoxynivalenol) in ppm before and after removal of Fusarium damaged kernels.

These results are graphically presented in FIG. 7, where C 1-C 10 are referred to as Cargil 1-Cargil 10.

The method removes all or nearly all visibly infected kernels. In general, the infection is dramatically reduced as a result. However, visually healthy kernels, which will not be removed from an infected sample, may contain fusarium and thus mycotoxin to an uncertain extent, which is typically less than 1 ppm, in these particular kernels. Nevertheless of eleven samples between 1 and 5 ppm DON, nine were reduced to less than 0.5 ppm and the other two (107 and 256-5) to less than 1 ppm. The sole sample between 0.5 and 1 ppm (174) was reduced to less than 0.5 ppm. Eleven samples between 0 and 0.5 ppm were usually reduced, the four anomalies were ascribed to sampling error after removal. Two samples with over 10 ppm were reduced to 5 ppm or less. It was concluded that the method was effective in reducing infected kernels and DON. In practice previously rejected grain would be tested for mycotoxin after kernel removal, and (re)graded accordingly.

The values of the amplitude at each wavelength for each pulse of the strobing sequence for an individual kernel are measured at 566 Hz to 2500 Hz.

Samples of selected infected and healthy kernels were then compared. The amplitudes are then summed separately for each kernel and wavelength. These amplitudes can be compared as a data vector in this case against calibrated values of healthy and infected kernels by linear discriminant analysis. Principal component analysis may also be applied.

Linear discriminant analysis used the summed amplitudes to indicate whether kernels were healthy or infected. Principal component analysis compared the amplitudes weighted statistically to derive a scalar value indicative of healthy or infected kernels.

Figure 8:
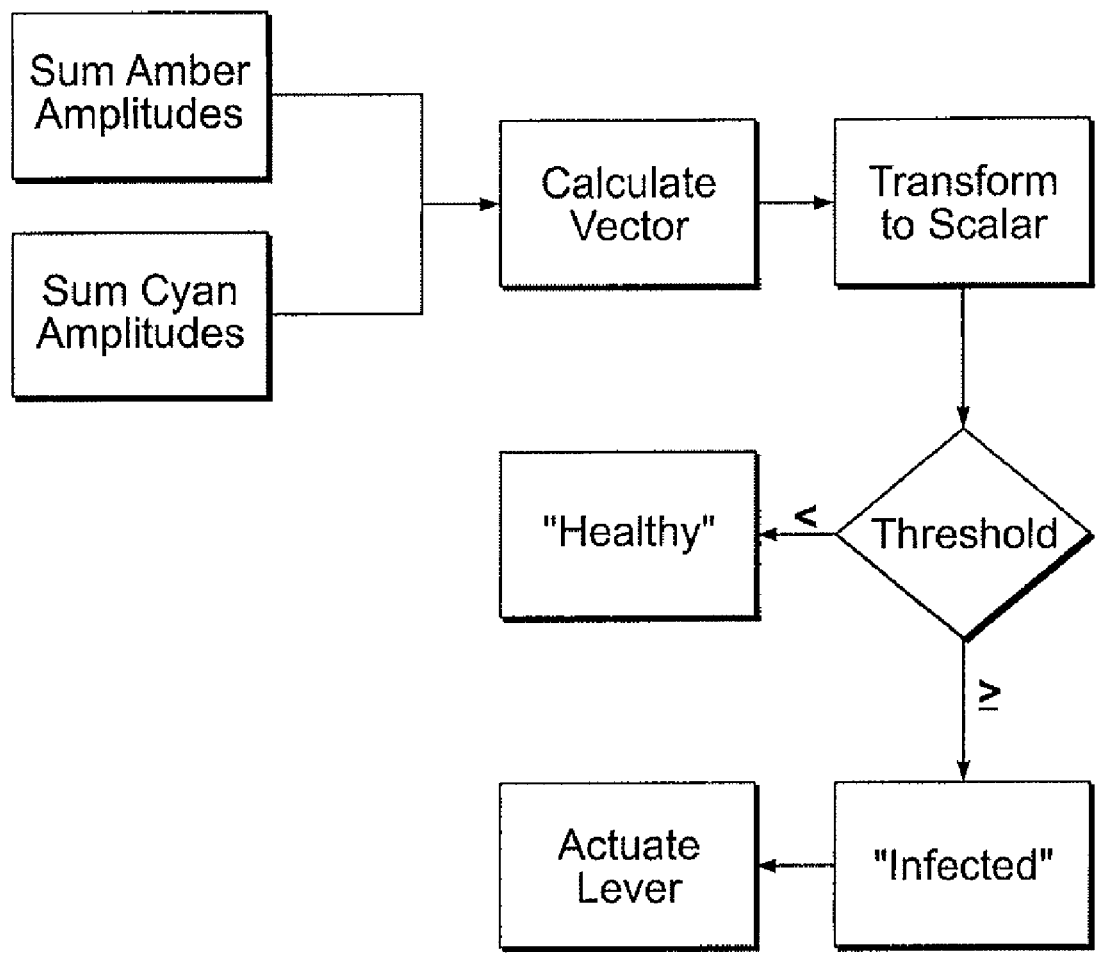
FIG. 8 shows an exemplary flow chart of an algorithm of the invention.

Both scalar value sets from linear discriminate analysis and principle component analysis gave two overlapping normal (gaussian) distributions with infected greater than healthy. A threshold value is set, if the value equalled or exceeded the threshold, the kernel was deemed infected and a logic signal sent to the appropriate rotary voice coil. While various threshold values are possible, the one selected rejected about 10% of visually healthy kernels and about 95% of visually infected kernels. Depending on the intensity of infection of individual kernels, more or less infected kernels will be rejected, while the proportion of healthy kernels rejected will vary less. A possible LDA implementation is shown in FIG. 8.

A calibration test of 288 visually healthy kernels gave 22, 7.6%, misclassified as "infected," while 288 visually infected kernels gave 19, 6.6%, misclassified as "healthy."

The samples tested were sorted using the same threshold value. Kernel data can be updated if desired, to refine the threshold criteria.

The above-described details, materials and components are meant as illustrative only and not in a limiting sense.

Further features of the invention are indicated. The angle of incidence of the light, preferably both light source and collector are angled between 30° and 60° to the tangent to the surface of the cylinder, with 45° preferred. In practice one version has the light source angled at about right angles to tangent of the surface of the cylinder, and the collector at about 45°. The light collector may have a collimator, comprised of two spherical lenses, but the clean end cut at right angles of a optical fibre, was effective. A lens system for the light collector at the photodiode end of the optical fibre was similarly found unnecessary, the end of the optical fibre, clean cut at right angles, may be fed directly into a pixel array of the photodiode. Alternatively a tapered end of an optical fibre can be fed directly onto a detecting pixel of the photodiode. When a lens or lens system is present it focuses light from one optical fibre onto a detecting pixel. A lens system may focus several optical fibres onto several different pixels. The microprocessor may comprise a field programmable gate array, which controls means to alternately strobe the wavelengths emitted by the light source. The microprocessor may comprise a dedicated computer, which controls means to alternately strobe the wavelengths emitted by the light source. The cylinder is preferably a substantially horizontal rotatable cylinder having an array of a plurality of apertures, each aperture sized to suctionally engage one kernel. The apertures are radially equispaced in a plane perpendicular to the axis of the cylinder and longitudinally equispaced parallel to the axis of the cylinder. A plurality of light sources each provide light to illuminate one kernel at two distinct wavelengths on the surface of the cylinder in second position. Each light collector transmits the light from one kernel to a light measuring device comprising at least one photodiode which measures the amplitude of the reflected and scattered light generated by one kernel at both wavelengths as electronic signals. A microprocessor compares the electronic signals as measured amplitudes at each wavelength for each said kernel and determines from said comparison whether said kernel meets infected criteria. The microprocessor, when said kernel meets infected criteria transmits a logic signal to actuate one of an array of levers spaced apart from said cylinder, each lever pivots about a lever axis, said lever axes are aligned parallel to the axis of the cylinder. The lever when actuated rotates to strike said infected kernel in third position and dislodge it to fall into said chute to receive infected kernels. There is scraper means in fourth position to dislodge healthy kernels to fall into said chute to receive healthy kernels. Preferably each lever is integral to a different rotary voice coil. Preferably there are means to alternately strobe both wavelengths emitted, which control the light sources. Each microprocessor may comprise a field programmable gate array, which controls means to alternately strobe said wavelengths emitted by said light source. Each microprocessor may comprise a dedicated computer, which controls means to alternately strobe said wavelengths emitted by said light source.

The invention claimed is:

1. A method for removing fusarium infected kernels from grain comprising:
    illuminating each said kernel with distinct first wavelength of light and a distinct second wavelengths of light, said first wavelength being selected from wavelengths reflected and scattered substantially the same by healthy and infected kernels, said second said wavelength being selected from wavelengths reflected and scattered significantly greater by infected kernels than healthy;
    measuring the amplitude of light reflected and scattered at each said wavelength by each said kernel;
    comparing the amplitude of the light reflected and scattered at said first wavelength to the amplitude of the light reflected and scattered at said second wavelength to determine if a criteria for an infected kernel is met; and
    rejecting said kernel when said criteria for an infected kernel is met.

2. The method of claim 1, wherein said wavelengths illuminating said kernel are alternately strobed, to produce a sequence of amplitudes of both wavelengths, which are transformed mathematically to give a single scalar value, which is then compared to a calibrated threshold scalar derived from statistical analysis of known healthy and infected kernels, to determine if the kernel is infected.

3. The method of claim 2, wherein said statistical analysis is principal component analysis.

4. The method of claim 2 wherein said statistical analysis is linear discriminant analysis.

5. The method of claim 2, wherein said first wavelength is 505 nm and said second wavelength is 590 nm.

6. An apparatus to separate fusarium infected kernels from healthy kernels of grain, comprising an input chute for grain, and separate output chutes for healthy and infected kernels, and
    comprising a rotatable cylinder having at least one aperture sized to suctionally engage one kernel,
    said grain input chute abutting the surface of said cylinder in first position,
    a light source to provide light to illuminate said kernel at two distinct wavelengths on the surface of said cylinder in second position, a first wavelength of said wavelengths being reflected and scattered substantially the same by healthy and infected kernels, a second wavelength of said wavelengths being reflected and scattered significantly differently by healthy and infected kernels, and means to alternately strobe said wavelengths of said light source,
    a light collector adjacent said light source for collecting said reflected and scattered light at both said wavelengths,
    said light collector transmitting said light to a light measuring device comprising at least one photodiode which measures the amplitude of said reflected and scattered light generated by said kernel at both said wavelengths as electronic signals;
    a microprocessor, which compares the electronic signals as measured amplitudes at each wavelength and determines from said comparison whether said kernel meets infected criteria;
    said microprocessor, when said kernel meets infected criteria transmitting a logic signal to actuate a lever integral to a rotary voice coil;

said lever when actuated rotating to strike an infected kernel in third position and dislodge it to fall into said chute to receive infected kernels; and scraper means in fourth position to dislodge a healthy kernel to fall into said chute to receive healthy kernels.

7. The apparatus of claim 6, wherein said light source comprises at least one optical fibre transmitting said wavelengths from a lightbox containing at least one LED generating said first wavelength and at least another LED generating said second wavelength to a lens system collimating and focussing said light to illuminate said kernel.

8. The apparatus of claim 6, wherein said microprocessor comprises a field programmable gate array, which controls means to alternately strobe said wavelengths emitted by said light source.

9. The apparatus of claim 6, wherein said light measuring device receives said light collector onto a plurality of detecting pixels to measure the amplitude of the light.

10. The apparatus of claim 8, wherein there is an encoder wheel co-axial with said cylinder, said encoder wheel having at least one aperture therein, and aligned with said aperture an LED and a photodiode, light passing through said aperture from said LED said photodiode, and said photodiode transmitting a signal to said means to alternately strobe said wavelengths said light source, and initiate an alternate strobing sequence.

* * * * *